United States Patent [19]
Kolff

[11] Patent Number: 5,332,403
[45] Date of Patent: Jul. 26, 1994

[54] LVAD WITH T-SHAPE AND UNIDIRECTIONAL VALVE

[76] Inventor: Jack Kolff, 1 Lauren La., Johnstown, Pa. 15905-4803

[21] Appl. No.: 930,186

[22] Filed: Aug. 17, 1992

[51] Int. Cl.[5] .............................................. A61F 2/22
[52] U.S. Cl. ......................................... 623/3; 623/2; 600/16
[58] Field of Search ..................... 600/16; 623/2, 3, 1

[56] References Cited

U.S. PATENT DOCUMENTS

| | | | |
|---|---|---|---|
| 2,127,903 | 5/1936 | Bowen | 623/1 |
| 3,683,926 | 8/1972 | Suzuki | 623/1 |
| 3,765,032 | 10/1973 | Palma | 623/1 |
| 4,034,732 | 7/1977 | Thoma | 623/3 |
| 4,994,077 | 2/1991 | Dobben | 623/2 |

*Primary Examiner*—David Isabella
*Assistant Examiner*—Debra S. Brittingham
*Attorney, Agent, or Firm*—Thorpe, North & Western

[57] ABSTRACT

A ventricular assist device comprises an artificial ventricle including a blood compartment, a pumping compartment and a pumping membrane separating the respective blood and pumping compartments. A connecting T-shaped conduit is attached to the artificial ventricle and includes an interconnected verticle leg portion and a horizontal portion with flow communication therebetween. The T-shaped conduit is coupled at a free end of the leg portion to the blood compartment of the artificial ventricle, the horizontal portion of the T-shaped conduit includes opposing open ends which are formed along an axial flow line. A unidirectional valve is positioned near one end of the horizontal portion of conduit for limiting blood flow to a single direction at the valved end, the remaining end of the horizontal portion remaining open and unobstructed and capable of receiving blood flow from an attached natural ventricle. The ventricle assist device includes a conduit for coupling the pumping chamber of the artificial ventricle to a pumping source capable of powering the artificial ventricle with periodic pumping action. A method of implantation is also disclosed.

10 Claims, 2 Drawing Sheets

5,332,403

LVAD WITH T-SHAPE AND UNIDIRECTIONAL VALVE

BACKGROUND OF THE INVENTION

1. Field of the Invention

The invention relates to intracorporeal left ventricular assist devices (LVADs).

2. Prior Art

Typically, LVADs which go from the left ventricle or the left atrium to the aorta need two valves to control both inflow and outflow of blood. These valves are unidirectional valves which maintain the direction of blood flow toward the peripheral circulation, or in other desired flow directions. Examples of these types of LVADs include an LVAD which is connected through a single opening in the aorta as described by Shlomo Gabbay and which is inserted just above the aortic valve, high up in the ascending aorta. Another type of LVAD in this family was developed by Dr. John Nanas of Greece and is inserted in the abdominal aorta. Other types of LVADs take blood from the aorta and pump it back into the aorta and might better be called counterpulsating devices. The filling phase in this type of device occurs during the left ventricle systole, with blood being expelled during left ventricular diastole.

The use of two valves has generally been seen as an essential part of the LVAD which is necessary to provide unidirectional blood flow. It is also known that valves are often the most expensive element of an LVAD, and are also the most vulnerable to fail and/or serve as a site for blood clotting. Accordingly, prior art LVADs have been expensive and offer a substantial risk to the patient with respect to valve failure or other adverse conditions with respect to the blood.

OBJECTS AND SUMMARY OF THE INVENTION

It is an object of the present invention to provide an improved LVAD which uses only one valve, and thereby reduces cost and risks associated therewith.

It is a further object of this invention to provide an LVAD which may be quickly inserted through a single cut in the aorta, thereby reducing cost and complexity of implantation.

These and other objects are realized in a ventricle assist device which comprises an artificial ventricle including a blood compartment, a pumping compartment and a pumping membrane separating the respective blood and pumping compartments. A T-shaped conduit having an interconnected vertical leg portion and horizontal portion with flow communication therebetween is coupled at a free end of the leg portion to the blood compartment. The horizontal portion includes opposing open ends formed along an axial flow line, which are adapted for connection within the circulatory system of a patient in common blood flow. A unidirectional valve is positioned near one end of the horizontal portion of conduit for limiting blood flow to a single direction at the valved end. The remaining end of the horizontal portion remains open and unobstructed and capable of receiving blood flow to and from the artificial ventricle. Means is provided for coupling the pumping compartment of the ventricle to a pumping source capable of powering the ventricle with periodic pumping action.

Other objects and features of the present invention will be apparent to those skilled in the art, in view of the following detailed description, taken in combination with the accompanying drawings.

DETAILED DESCRIPTION OF THE INVENTION

Figure 1:
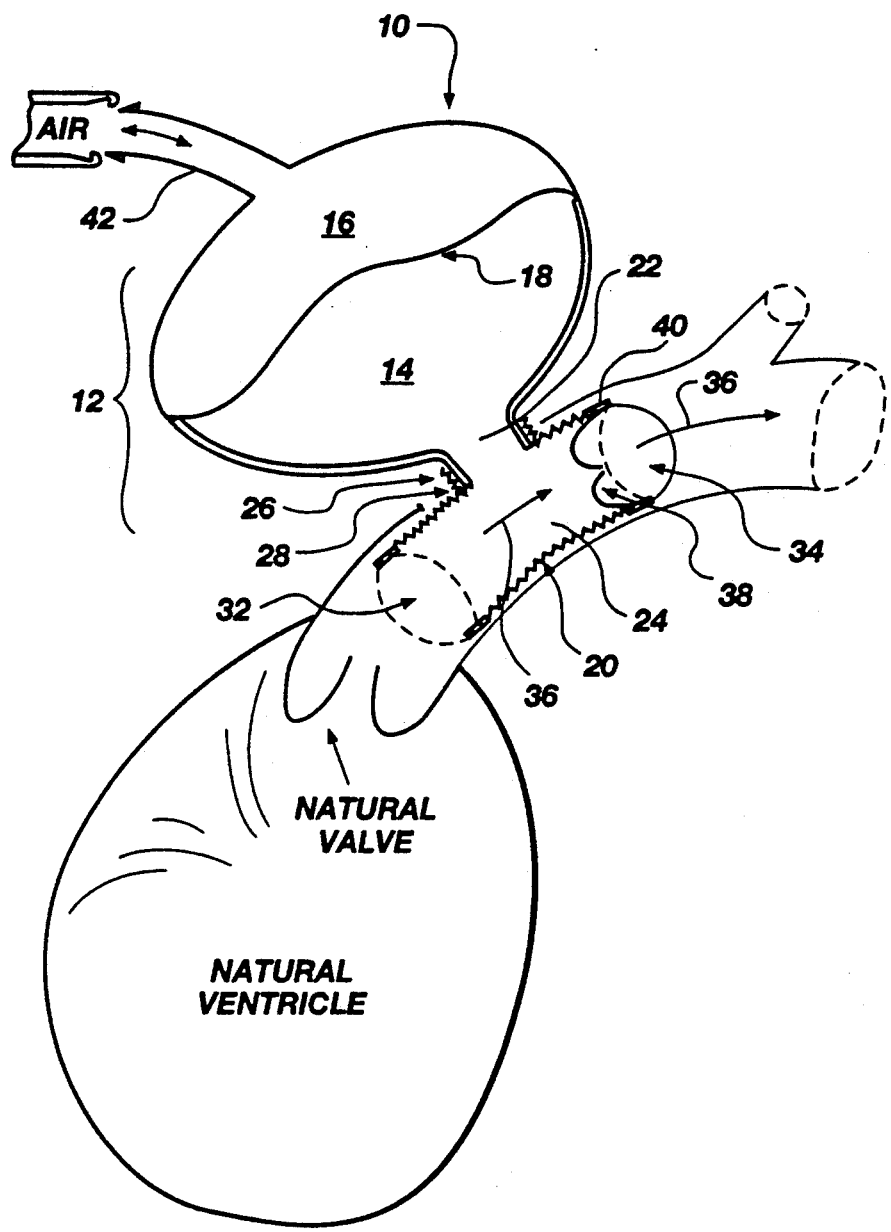
FIG. 1 shows a graphic, perspective view of an LVAD inserted at the aorta and attached natural ventricle, embodying the features of the present invention.

A ventricle assist device 10 in accordance with the present invention is shown in FIG. 1. It includes an artificial ventricle 12 including a blood compartment 14, a pumping compartment 16 and a pumping membrane 18 which separates the respective blood and pumping compartments. Such artificial ventricles are well known in the art and may be fabricated of numerous materials and in a variety of configurations. Further description of the ventricle is therefore deemed unnecessary.

A T-shaped conduit 20 is connected to the blood compartment 14 to provide a flow path for blood to and from the artificial ventricle and to the aorta of the patient. Specifically, the T-shaped conduit 20 has an interconnected vertical leg portion 22 and a horizontal portion 24 with flow communication therebetween. Conduit diameters are selected to ensure required flow capacity based on the extent of pumping action to be provided. Here again, materials may be selected from conventional compositions such as polyurethane.

The free end 26 of the vertical leg portion 22 is directly coupled to the blood compartment 14 by conventional sealing techniques. The other end of the vertical leg 22 connects to the horizontal portion at 28. The horizontal portion has opposing open ends 32 and 34 which fall along an axial flow line 36. This horizontal portion is adapted for connection within the circulatory system of a patient in common blood flow therewith.

A unidirectional valve 38 is positioned near one end of the horizontal portion of conduit for limiting blood flow to a single direction at the valved end. This valve is shown as a tricusp semi-lunar valve, but could be of other configurations as well. The valve is attached within a rigid ring 40 which is retained within the conduit. This ring 40 provides a location to secure the conduit within the aorta, as well as support the valve.

The remaining end of the horizontal portion is open and unobstructed and capable of receiving blood flow to and from the artificial ventricle.

Connecting means 42 is provided for coupling the pumping compartment 16 of the ventricle to a pumping source (not shown) which is capable of powering the ventricle with periodic pumping action. This may be either a pneumatic, liquid, electronic or magnetic pumping system as is customarily employed to displace the pumping diaphragm 16 to simulate pumping action of the heart. As will be noted later, this pumping action may be of a counter-pulsatile mode where the natural heart is somewhat operational, or may be the primary pumping force applied in cases of total ventricle failure.

Figure 2:
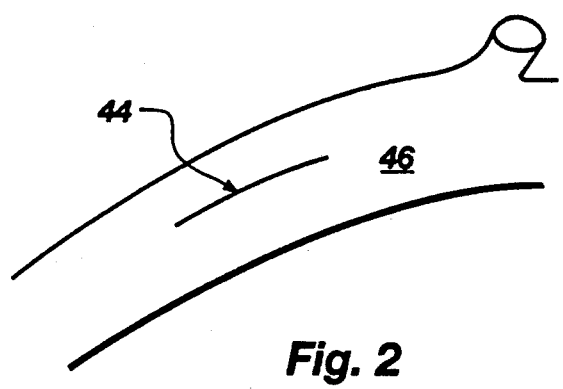
FIG. 2 graphically illustrates a segment of natural aorta which includes a slotted opening for receiving the assist device of the present invention.
Figure 3:
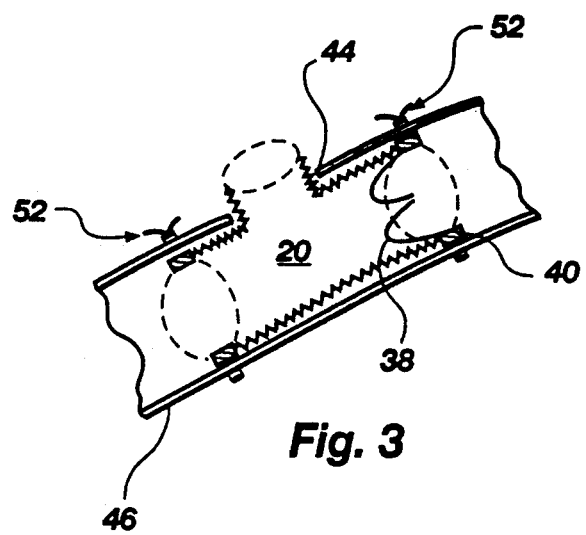
FIG. 3 shows a graphic cross section of the T conduit portion inserted within the aorta.
Figure 4:
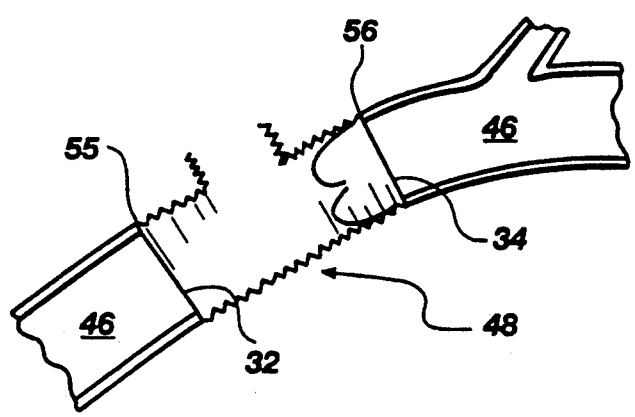
FIG. 4 illustrates an alternative implacement of the T conduit as a segment formed between severed ends of the aorta.

As shown in the preferred embodiment, the T-shaped conduit is structured for insertion within a slit 44 within the aorta 46 of a patient as shown in FIGS. 2 and 3. The vertical portion of the conduit is sized for extending through the slit for attachment to the artificial ventricle. Alternatively, FIG. 4 depicts that the T-shaped conduit may be sized for emplacement as an interconnecting section 48 between open ends 55 and 56 of natural aorta with each respective ends 32 and 34 of the horizontal portion being coupled to opposing openings within the aorta. In this case, the ends of the conduit may be either sutured in place, or be sealed by the more convenient technique of using a draw string or tie 52 around the aorta and rigid interior ring as shown in FIG. 3. In either instance, the horizontal portion of the T-shaped conduit is configured for placement within the circulatory system with the axial flow in alignment with axial flow of the circulatory system.

In the preferred embodiment disclosed, the unidirectional valve is configured only for outflow of blood, thereby adapting the device for emplacement within the aorta just above the aortic valve using the natural aortic valve as the "inflow" valve for the assist device. This enables use of the ventricle assist device without need for additional artificial valving, and thereby provides the reduced risk and cost as mentioned earlier. When the device is coupled to the aorta of a ventricle in complete failure, the area in the aorta between the aortic valve and the unidirectional valve is continuous and unobstructed, with the natural aortic valve operating as an inflow valve and the unidirectional valve operating as the outflow valve to this area. In this case, the ventricle in failure operates as merely a reservoir for blood.

If the left ventricle is not entirely in failure, the LVAD would be operated in a counter-pulsatile mode. The weak contraction of the left ventricle acts like an atrial contraction filling the LVAD during diastole of the LVAD. During systole of the LVAD the aortic valve is closed. The natural left ventricle can be filled by its own diastole and by the atrial contraction of the natural atrium if there is such, as well as by the blood pressure of the venous return.

The foregoing invention is practiced within a methodology which is characterized by the following general steps. First, a slit 44 is made in a great artery (pulmonary artery or aorta) of the patient. Next, a horizontal portion 24 of the T-shaped conduit 20 is inserted within the artery. This horizontal section 24 includes the unidirectional valve 38 at one end as described above. This T-shaped conduit is coupled at a vertical leg 22 thereof to an artificial ventricle 10 which supplies pumping power to the entrained blood. The slit around the T-shaped conduit is then sealed 52 to prevent blood flow from the circulatory system except through the T-shaped conduit. The system is operated by pumping the artificial ventricle.

It is to be understood that the foregoing detailed description is given by way of example, and is not to be considered limiting this respect to the claims that follow.

I claim:

1. A ventricular assist device comprising:
   an artificial ventricle including a blood compartment, a pumping compartment and a pumping membrane separating the respective blood and pumping compartments;
   a connecting, T-shaped conduit having an interconnected vertical leg portion and a horizontal portion with flow communication therebetween and being coupled at a free end of the leg portion to the blood compartment, said horizontal portion having opposing open ends formed along an axial flow line, one of said opposing open ends including a rigid ring attached to the conduit, said horizontal portion being adapted for connection within the circulatory system of a patient in common blood flow;
   a unidirectional valve coupled to the rigid ring and positioned within and near one end of the horizontal portion of conduit for limiting blood flow to a single direction at the valved end, the remaining end of the horizontal portion remaining open and unobstructed and capable of receiving blood flow from an attached natural ventricle; and
   means for coupling the pumping compartment of the artificial ventricle to a pumping source capable of powering the artificial ventricle with periodic pumping action.

2. A device as defined in claim 1, wherein the T-shaped conduit is structured for insertion within a slit within the aorta of a patient, said vertical portion being sized for extending through the slit for attachment to the artificial ventricle.

3. A device as defined in claim 1, wherein the unidirectional valve is configured only for outflow of blood, thereby adapting the device for emplacement within the aorta just above the aortic valve as a ventricular assist device without need for additional artificial valving.

4. A device as defined in claim 3, wherein the open end of the horizontal portion includes a rigid ring enabling the aorta to be secured around the rigid ring, said unidirectional valve being positioned in a rigid ring contained within the opposing end of the horizontal portion.

5. A device as defined in claim 1, wherein the T-shaped conduit is sized for emplacement as an interconnecting section of natural aorta of the patient with each respective end of the horizontal portion between coupled to opposing openings within the aorta.

6. A device as defined in claim 1, wherein the horizontal portion of the T-shaped conduit is inserted within a slit within the aorta of a patient, said vertical portion extending through the slit for attachment to the artificial ventricle.

7. A device as defined in claim 1, wherein the unidirectional valve is configured for outflow of blood and the horizontal portion is positioned within the aorta of the patient just above the aortic valve as a ventricular assist device without additional artificial valving.

8. A device as defined in claim 7, wherein the open end of the horizontal portion includes a rigid ring enabling the aorta to be secured around the rigid ring, said unidirectional valve being positioned in a rigid ring contained within the opposing end of the horizontal portion, each of said ends of the horizontal portion being tied within the aorta to seal blood flow within the device.

9. A device as defined in claim 7, wherein the device is coupled to the aorta of a ventricle in failure, the area in the aorta between the aortic valve and the unidirectional valve being continuous and unobstructed, said natural aortic valve operating as an inflow valve and the unidirectional valve operating as the outflow valve to this area, said ventricle in failure operating as merely a reservoir for blood.

10. A device as defined in claim 1, wherein the horizontal portion of the T-shaped conduit is configured for placement within the circulatory system with the axial flow in alignment with axial flow of the circulatory system.

* * * * *